United States Patent [19]

Petersen et al.

[11] Patent Number: 4,544,658

[45] Date of Patent: Oct. 1, 1985

[54] 1-CYCLOPROPYL-6-FLUORO-1,4-DIHYDRO-4-OXO-7-(ALKYL-1-PIPERAZINYL)-QUINOLINE-3-CARBOXYLIC ACIDS, PROCESSES FOR THEIR PREPARATION AND ANTIBACTERIAL AGENTS CONTAINING THEM

[75] Inventors: Uwe Petersen, Leverkusen; Klaus Grohe, Odenthal; Hans-Joachim Zeiler, Velbert; Karl G. Metzger, Wuppertal, all of Fed. Rep. of Germany

[73] Assignee: Bayer Aktiengesellschaft, Leverkusen, Fed. Rep. of Germany

[21] Appl. No.: 560,027

[22] Filed: Dec. 9, 1983

[30] Foreign Application Priority Data

Dec. 29, 1982 [DE] Fed. Rep. of Germany ....... 3248506

[51] Int. Cl.$^4$ ................... A61K 31/47; A61K 31/495; C07D 401/04
[52] U.S. Cl. .................................... 514/254; 544/358; 544/363; 544/404; 546/156
[58] Field of Search .......................... 544/363; 424/250

[56] References Cited

U.S. PATENT DOCUMENTS 3,149,104  9/1964  Lesher et al. ...................... 544/362

OTHER PUBLICATIONS

Takase et al., "Chemical Abstracts", vol. 93, 1980, col. 93:168301t and col. 93:168305x.

Primary Examiner—Glennon H. Hollrah
Assistant Examiner—James H. Turnipseed
Attorney, Agent, or Firm—Sprung, Horn, Kramer & Woods

[57] ABSTRACT

The invention relates to 1-cyclopropyl-6-fluoro-1,4-dihydro-4-oxo-7-(alkyl-1-piperazinyl)quinoline-3-carboxylic acids of Formula (I), processes for their manufacture, compositions containing them and use of said compounds and compositions as antibacterial and/or feedstuff additives.

16 Claims, No Drawings

1-CYCLOPROPYL-6-FLUORO-1,4-DIHYDRO-4-OXO-7-(ALKYL-1-PIPERAZINYL)QUINOLINE-3-CARBOXYLIC ACIDS, PROCESSES FOR THEIR PREPARATION AND ANTIBACTERIAL AGENTS CONTAINING THEM

The present invention relates to new 1-cyclopropyl-6-fluoro-1,4-dihydro-4-oxo-7-(alkyl-1-piperazinyl)-quinoline-3-carboxylic acids, processes for their preparation and antibacterial agents and feedstuff additives containing them.

It has already been disclosed that 1-ethyl-6-fluoro-1,4-dihydro-4-oxo-7-(1-piperazinyl)quinoline-3-carboxylic acid (Norfloxacin) has antibacterial properties (J.Med.Chem. 23, 1358 (1980)).

It has now been found that the new 1-cyclopropyl-6-fluoro-1,4-dihydro-4-oxo-7-(alkyl-1-piperazinyl)quinoline-3-carboxylic acids of the formula (I)

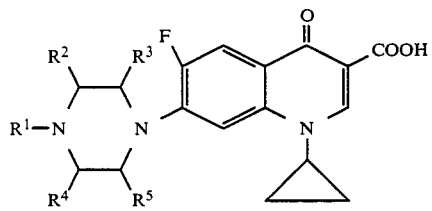

in which
- $R^1$ represents hydrogen or alkyl which is optionally substituted by 1 to 2 hydroxyl and has 1 to 12, preferably 1 to 4, carbon atoms,
- $R^2$, $R^3$, $R^4$ and $R^5$ are identical or different and represent hydrogen or alkyl having 1 to 4, preferably 1 to 2, carbon atoms, at least one of the radicals $R^2$ to $R^5$ denoting alkyl, and their pharmaceutically utilisable acid addition, alkali metal and alkaline earth metal salts and hydrates have high antibacterial activity.

Moreover, it has been found that the 1-cyclopropyl-6-fluoro-1,4-dihydro-4-oxo-7-(alkyl-1-piperazinyl)-quinoline-3-carboxylic acids of the formula (I) are obtained when 7-chloro-1-cyclopropyl-6-fluoro-1,4-dihydro-4-oxoquinoline-3-carboxylic acid of the formula (II)

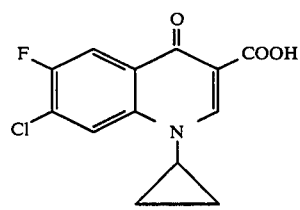

is reacted, optionally in the presence of an acid-binding agent, with a piperazine derivative of the formula (III)

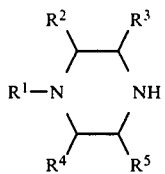

in which
- $R^1$, $R^2$, $R^3$, $R^4$ and $R^5$ have the meanings indicated above, (method A).

The compounds according to the invention can also be obtained by reacting a compound of the formula (IA) (=I, $R^1$=H)

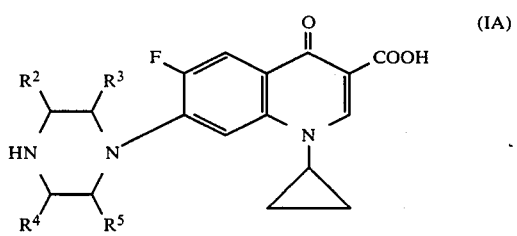

in which
- $R^2$, $R^3$, $R^4$ and $R^5$ have the meaning indicated above, with a compound of the formula (IV)

$$R^1-X \quad (IV)$$

in which
- $R^1$ has the meaning indicated above other than hydrogen, and
- X denotes chlorine, bromine or iodine, in the presence of an acid-binding agent (method B).

Surprisingly, the compounds according to the invention not only show higher antibacterial activity than the compounds known from the state of the art but they also show a markedly better absorbability. Thus they are suitable as active compounds for veterinary medicine, veterinary medicine being taken to include prophylaxis and treatment of fishes. Thus the substances according to the invention represent an enrichment of pharmacy.

When, in the reaction by method A, 2-methylpiperazine and 7-chloro-1-cyclopropyl-6-fluoro-1,4-dihydro-4-oxoquinoline-3-carboxylic acid are used as the starting materials, the course of the reaction can be represented by the following diagram:

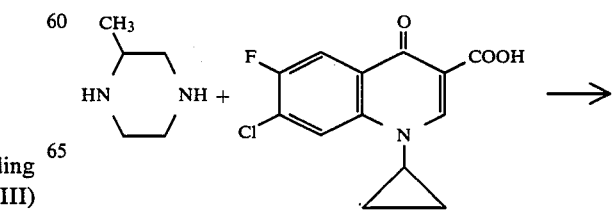

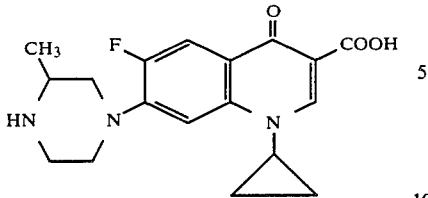

When, in the reaction by method B, ethyl iodide and 1-cyclopropyl-6-fluoro-1,4-dihydro-4-oxo-7-(3-methyl-1-piperazinyl)quinoline-3-carboxylic acid are used as the starting materials, the course of the reaction can be represented by the following diagram:

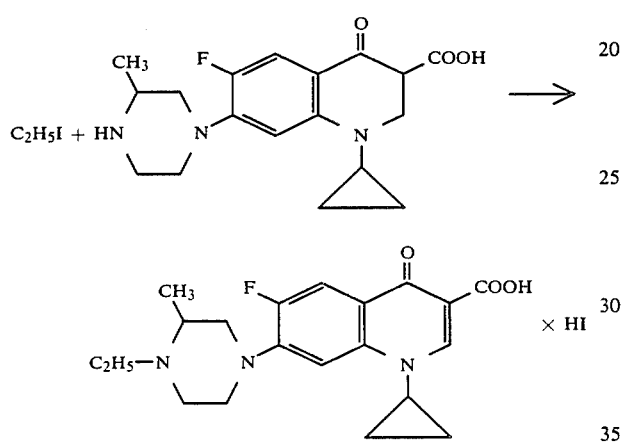

The 7-chloro-1-cyclopropyl-6-fluoro-1,4-dihydro-4-oxoquinoline-3-carboxylic acid of the formula (II) utilisable as the starting material by method A can be prepared in accordance with the following reaction diagram:

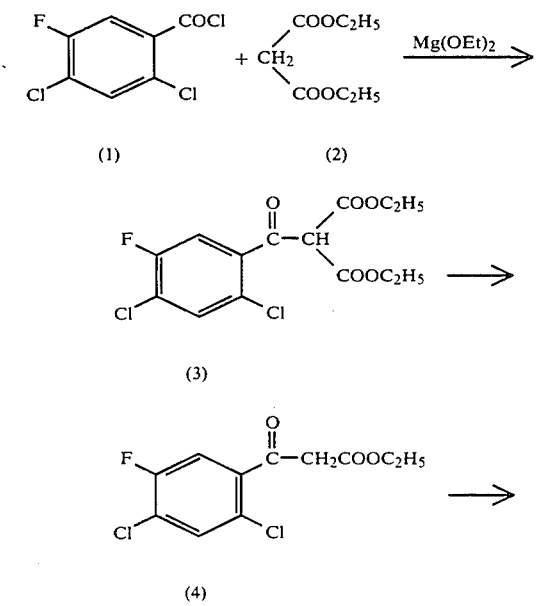

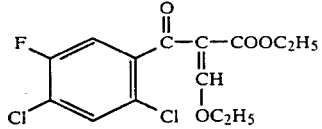

(5)

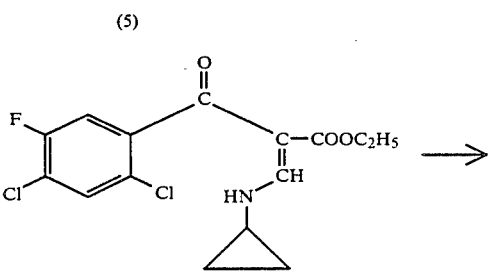

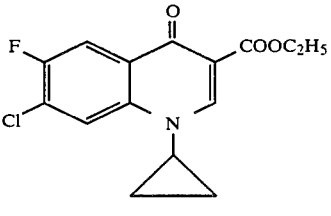

(7)

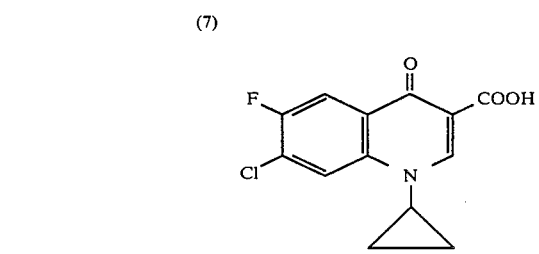

According to this, diethyl malonate (2) is acylated with (1) in the presence of magnesium alcoholate with 2,4-dichloro-5-fluorobenzoyl chloride (German Patent Application No. 3,142,856.8) to give the acyl malonate (3) (Organikum, 3rd edition, 1964, page 438).

By partial hydrolysis and decarboxylation of (3) in an aqueous medium with catalytic amounts of sulphuric acid or p-toluenesulphonic acid, the ethyl aroylacetate (4) is obtained in good yield and this is converted with triethyl orthoformate/acetic anhydride into ethyl 2-(2,4-dichloro-5-fluorobenzoyl)-3-ethoxyacrylate (5). Reaction of (5) with cyclopropylamine in a solvent, such as, for example, methylene chloride, ethanol, chloroform, cyclohexane or toluene, leads, in a slightly exothermic reaction, to the desired intermediate (6).

The cyclisation reaction (6)→(7) is carried out in the temperature range from about 60° to 300° C., preferably 80° to 180° C.

Dioxane, dimethyl sulphoxide, N-methylpyrrolidone, sulpholane, hexamethylphosphoric triamide and, preferably, N,N-dimethylformamide can be used as the diluent.

Suitable acid-binding agents for this reaction step are potassium tert.-butanolate, butyllithium, lithium phenyl, phenyl magnesium bromide, sodium methylate, sodium hydride and, particularly preferably, potassium carbonate or sodium carbonate. It can be advantageous to employ an excess of 10 mol % of base.

The ester hydrolysis under basis or acid conditions taking place in the last step leads to the 7-chloro-1-cyclopropyl-6-fluoro-1,4-dihydro-4-oxoquinoline-3-carboxylic acid II.

The 2,4-dichloro-5-fluorobenzoyl chloride (1) used as starting material for this synthetic route, and the corresponding carboxylic acid, as well as the 3-fluoro-4,6-dichlorotoluene (10) required for the preparation of (1) are not yet known.

The diagram below shows the preparation of these precursors or intermediates, starting from 2,4-dichloro-5-methylaniline (8).

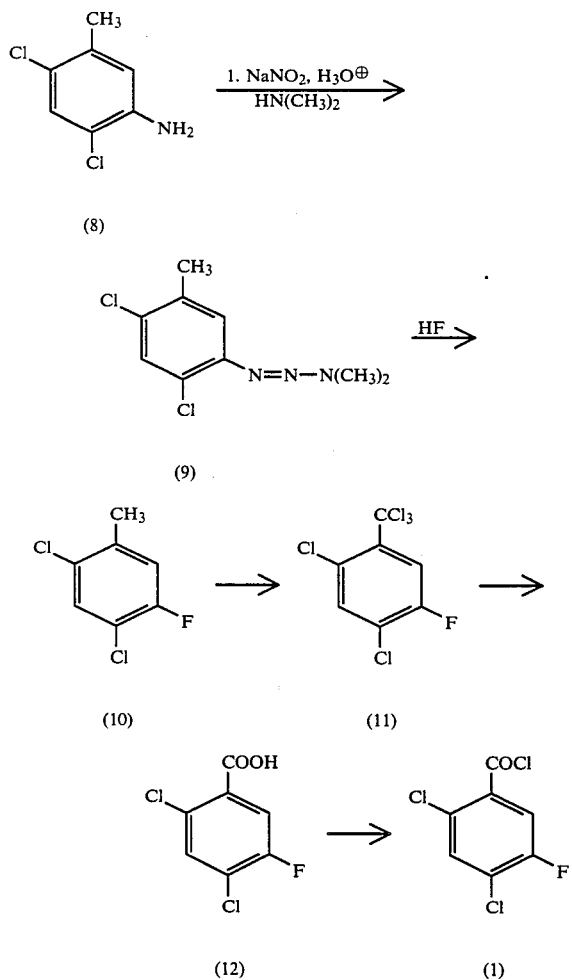

According to this, 2,4-dichloro-5-methylaniline (8) is diazotised using $NaNO_2$ and the diazonium salt thereby produced is converted into the triazene (9) with dimethylamine.

The triazene (9) is dissolved in excess anhydrous HF. This cleaves the triazene into 2,4-dichloro-5-methyldiazonium fluoride and dimethylamine. Without intermediate isolation, this solution is thermally cleaved at 130° to 140° C., with elimination of $N_2$, to give 3-fluoro-4,6-dichlorotoluene (10). Yield: 77.7% of theory.

The 3-fluoro-4,6-dichlorotoluene (10) is chlorinated under UV irradiation in the temperature range from 110° to 160° C. to give 2,4-dichloro-5-fluoro-1-trichloromethylbenzene (11).

Hydrolysis of (11) with 95% strength sulphuric acid leads to 2,4-dichloro-5-fluorobenzoic acid (12) which is converted into the carbonyl chloride (1) (boiling point 121° C./20 mbar; $n_D^{20}$ 1.5722) with thionyl chloride.

The piperazine derivatives III used as starting materials are known or can be obtained by processes known from the literature. The following may be mentioned as examples:

2-Methylpiperazine, 1,2-dimethylpiperazine, cis- and trans-2,5-dimethylpiperazine, cis- and trans-2,6-dimethylpiperazine, 2,3-dimethylpiperazine, 2,3,5-trimethylpiperazine, 2,3,5,6-tetramethylpiperazine, 2-ethylpiperazine, 2-ethyl-3,6-dimethylpiperazine, 2-propylpiperazine, 2-isopropylpiperazine and 2-isobutylpiperazine.

The alkyl halides IV used as starting materials are known. The following may be mentioned as examples:

Methyl iodide, methyl bromide, ethyl iodide, ethyl bromide, ethyl chloride, 2-hydroxyethyl chloride, 3-hydroxypropyl chloride, 4-hydroxybutyl chloride, n-propyl bromide, i-propyl iodide, n-butyl bromide, i-butyl bromide, sec.-butyl chloride, n-pentyl chloride, 3-methylbutyl chloride and n-dodecyl chloride.

The reaction of II with III according to method A is preferably carried out in a diluent, such as dimethyl sulphoxide, N,N-dimethylformamide, hexamethylphosphoric triamide, sulpholane, water, an alcohol, such as methanol, ethanol, n-propanol, isopropanol or glycol monomethyl ether, or pyridine. Mixtures of these diluents can likewise be used.

All customary inorganic and organic acid-binding agents can be used as the acid-binding agent. These preferably include the alkali metal hydroxides, alkali metal carbonates, organic amines and amidines. The following may be specifically mentioned as particularly suitable: triethylamine, 1,4-diazabicyclo[2.2.2]octane (DABCO), excess piperazine derivative III or 1,8-diazabicyclo[5.4.0]undec-7-ene (DBU).

The reaction tempratures can be varied within a relatively wide range. In general, the process is carried out between about 20° and 200° C., preferably between 80° and 180° C.

The reaction can be carried out under normal pressure, but also under elevated pressure. In general, the reaction is carried out under pressures between about 1 and about 100 bar, preferably between 1 and 10 bar.

In carrying out the process according to the invention, 1 to 15 mols, preferably 1 to 6 mols, of the piperazine derivative III are employed to 1 mol of the carboxylic acid II.

The reaction of IA with IV is preferably carried out in a diluent, such as dimethyl sulphoxide, dioxane, N,N-dimethylformamide, hexamethylphosphoric triamide, sulpholane, water, an alcohol, such as methanol, ethanol, n-propanol, isopropanol or glycol monomethyl ether, or pyridine. Mixtures of these diluents can likewise be used.

All customary inorganic and organic acid-binding agents can be used as the acid-binding agent. These preferably include the alkali metal hydroxides, alkali metal carbonates, organic amines and amidines. The following may be specifically mentioned as particularly suitable: triethylamine, 1,4-diazabicyclo[2.2.2]octane DABCO) or 1,8-diazabicyclo[5.4.0]undec-7-ene (DBU).

The reaction temperatures can be varied within a relatively wide range. In general, the process is carried out between about 20° and about 180° C., preferably between 40° and 110° C.

The reaction can be carried out under normal pressure, but also under elevated pressure. In general, the reaction is carried out under pressures between about 1 and about 100 bar, preferably between 1 and 10 bar.

In carrying out the process according to the invention according to method B, 1 to 4 mols, preferably 1 to 1.5 mols, of the alkylating agent IV is used for 1 mol of compound IA.

The following, which can be prepared as described above or as described in the working examples, may be specifically mentioned as new active compounds: 1-cyclopropyl-6-fluoro-1,4-dihydro-4-oxo-7-(3-methyl-1-piperazinyl)quinoline-3-carboxylic acid, 1-cyclopropyl-6-fluoro-1,4-dihydro-4-oxo-7-(3,4-dimethyl-1-piperazinyl)quinoline-3-carboxylic acid, 1-cyclopropyl-6-fluoro-1,4-dihydro-4-oxo-7-(4-ethyl-3-methyl-1-piperazinyl)quinoline-3-carboxylic acid, 1-cyclopropyl-6-fluoro-1,4-dihydro-4-oxo-7-[4-(2-hydroxyethyl)-3-methyl-1-piperazinyl]quinoline-3-carboxylic acid, 1-cyclopropyl-6-fluoro-1,4-dihydro-4-oxo-7-[4-(3-hydroxypropyl)-3-methyl-1-piperazinyl]quinoline-3-carboxylic acid, 1-cyclopropyl-6-fluoro-1,4-dihydro-4-oxo-7-(2,5-dimethyl-1-piperazinyl)quinoline-3-carboxylic acid, 1-cyclopropyl-6-fluoro-1,4-dihydro-4-oxo-7-(2,4,5-trimethyl-1-piperazinyl)quinoline-3-carboxylic acid, 1-cyclopropyl-6-fluoro-1,4-dihydro-4-oxo-7-(4-ethyl-2,5-dimethyl-1-piperazinyl)quinoline-3-carboxylic acid, 1-cyclopropyl-6-fluoro-1,4-dihydro-4-oxo-7-(3,5-dimethyl-1-piperazinyl)quinoline-3-carboxylic acid, 1-cyclopropyl-6-fluoro-1,4-dihydro-4-oxo-7-(3,4,5-trimethyl-1-piperazinyl)quinoline-3-carboxylic acid, 1-cyclopropyl-6-fluoro-1,4-dihydro-4-oxo-7-(4-ethyl-3,5-dimethyl-1-piperazinyl)quinoline-3-carboxylic acid, 1-cyclopropyl-6-fluoro-1,4-dihydro-4-oxo-7-(3-ethyl-1-piperazinyl)quinoline-3-carboxylic acid, 1-cyclopropyl-6-fluoro-1,4-dihydro-4-oxo-7-(3-n-propyl-1-piperazinyl)quinoline-3-carboxylic acid, 1-cyclopropyl-6-fluoro-1,4-dihydro-4-oxo-7-(3-isopropyl-1-piperazinyl)quinoline-3-carboxylic acid, 1-cyclopropyl-6-fluoro-1,4-dihydro-4-oxo-7-(3-isobutyl-1-piperazinyl)quinoline-3-carboxylic acid, 1-cyclopropyl-6-fluoro-1,4-dihydro-4-oxo-7-(3-methyl-4-n-propyl-1-piperazinyl)quinoline-3-carboxylic acid, 1-cyclopropyl-6-fluoro-1,4-dihydro-4-oxo-7-(3-methyl-4-isopropyl-1-piperazinyl)quinoline-3-carboxylic acid, 1-cyclopropyl-6-fluoro-1,4-dihydro-4-oxo-7-(4-n-butyl-3-methyl-1-piperazinyl)quinoline-3-carboxylic acid, 1-cyclopropyl-6-fluoro-1,4-dihydro-4-oxo-7-(4-isobutyl-3-methyl-1-piperazinyl)quinoline-3-carboxylic acid, 1-cyclopropyl-6-fluoro-1,4-dihydro-4-oxo-7-(4-sec.-butyl-3-methyl-1-piperazinyl)quinoline-3-carboxylic acid, 1-cyclopropyl-6-fluoro-1,4-dihydro-4-oxo-7-(4-tert.-butyl-3-methyl-1-piperazinyl)quinoline-3-carboxylic acid, 1-cyclopropyl-6-fluoro-1,4-dihydro-4-oxo-7-(3-methyl-4-n-pentyl-1-piperazinyl)quinoline-3-carboxylic acid and 1-cyclopropyl-6-fluoro-1,4-dihydro-4-oxo-7-(4-n-dodecyl-3-methyl-1-piperazinyl)quinoline-3-carboxylic acid and their pharmaceutically utilisable acid addition salts, alkali metal salts, alkaline earth metal salts or hydrates.

The compounds according to the invention exhibit a broad antibacterial spectrum against Gram-positive and Gram-negative organisms, particularly against enterobacteriaceae; in particular even against those which are resistant to a variety of antibiotics, such as, for example, penicillins, cephalosporins, aminoglycosides, sulphonamides and tetracylins.

The compounds according to the invention have low toxicity and a potent and broad antimicrobial efficacy. These properties make it possible to use them as chemotherapeutic active compounds in medicine and as substances for preserving inorganic and organic materials, in particular organic materials of all types, for example polymers, lubricants, dyes, fibres, leather, paper and wood, foodstuffs and water.

The compounds according to the invention are active against a very broad spectrum of microorganisms. Using them, Gram-negative and Gram-positive bacteria and bacterioid microorganisms can be controlled and the diseases caused by these pathogens can be treated.

The compounds according to the invention are particularly active against bacteria and bacterioid microorganisms. Thus they are particularly well suited for the chemotherapy of local and systemic infections caused by these pathogens in medicine.

For example, local and/or systemic diseases caused by the following pathogens or by mixtures of the following pathogens can be treated and/or prevented: Micrococcaceae, such as staphylococci, for example Staphylococcus aureus, Staph. Epidermidis, (Staph.=Staphylococcus); Lactobacteriaceae, such as streptococci, for example Streptococcus pyogenes, α- and β-haemolytic streptococci, non (γ-) haemolytic streptococci, enterococci and Diplococcus pneumoniae (pneumococci) (Str.=Streptococcus); Enterobacteriaceae, such as escherichiae bacteria of the coli group: escherichia bacteria, for example Escherichia coli, enterobacter bacteria, for example aerogenes, E. cloacae, Klebsiella bacteria, for example K. pneumoniae, serratia, for example Serratia marcescens (E.=Enterobacter) (K.=Klebsiella), proteae bacteria of the proteus group: proteus, for example Proteus vulgaris, Pr.morganii, Pr.rettgeri and Pr.mirabilis (Pr.=Proteus); pseudomonadaceae, such as pseudomonas bacteria, for example Pseudomonas aeruginosa (PS.=Pseudomonas); bacteroidaceae, such as bacteroides bacteria, for example Bacteroides fragilis (B.=Bacteroides); mycoplasma, for example Mycoplasma pneumonia.

The above list of pathogens is merely exemplary and should not by any means be interpreted as restrictive.

The following may be mentioned as examples of illness which can be treated by the compounds according to the invention: diseases of the respiratory tract and the pharyngeal cavity; otitis; pharyngitis; pneumonia; peritonitis; pyelonephritis; cystitis; endocarditis; systemic infections; bronchitis; arthritis; local infections and septic diseases.

The present invention includes pharmaceutical preparations which in addition to non-toxic, inert pharmaceutically suitable excipients contain one or more compounds according to the invention or which consist of one or more active compounds according to the invention, and processes for the production of these preparations.

The present invention also includes pharmaceutical preparations in dosage units. This means that the preparations are in the form of individual parts, for example tablets, dragees, capsules, pills, suppositories and ampoules, of which the content of active substance corresponds to a fraction or a multiple of an individual dose. The dosage units can contain, for example, 1, 2, 3 or 4 individual doses or ½, ⅓ or ¼ of an individual dose. An individual dose preferably contains the amount of active compound which is given in one administration and which usually corresponds to a whole, a half or a third or a quarter of a daily dose.

By non-toxic, inert pharmaceutically suitable excipients there are to be understood solid, semi-solid or liquid diluents, fillers and formulation auxiliaries of all kinds.

Tablets, dragees, capsules, pills, granules, suppositories, solutions, suspensions and emulsions, pastes, ointments, gels, creams, lotions, powders and sprays may be mentioned as preferred pharmaceutical preparations.

Tablets, dragees, capsules, pills and granules can contain the active compound or compounds alongside the customary excipients such as (a) fillers and extenders, for example starches, lactose, sucrose, glucose, mannitol and silica, (b) binders, for example carboxymethylcellulose, alginates, gelatine and polyvinylpyrrolidone, (c) humectants, for example glycerine, (d) disintegrating agents, for example agar-agar, calcium carbonate and sodium carbonate, (e) solution retarders, for example paraffin, and (f) absorption accelerators, for example quaternary ammonium compounds, (g) wetting agents, for example cetyl alcohol or glycerine monostearate, (h) adsorbents, for example kaolin and bentonite, and (i) lubricants, for example talc, calcium stearate and magnesium stearate and solid polyethylene glycols, or mixtures of the substances listed under (a) to (i).

The tablets, dragees, capsules, pills and granules can be provided with the customary coatings and shells, optionally containing opacifying agents, and can also be of such composition that they release the active compound or compounds only, or preferentially, in a certain part of the intestinal tract, optionally in a delayed manner, examples of embedding compositions which can be used being polymeric substances and waxes.

The active compound or compounds, optionally together with one or more of the abovementioned excipients, can also be in a micro-encapsulated form.

Suppositories can contain, in addition to the active compound or compounds, the customary water-soluble or water-insoluble excipients, for example polyethylene glycols, fats, for example cacao fat, and higher esters (for example $C_{14}$-alcohol with $C_{16}$-fatty acid) or mixtures of these substances.

Ointments, pastes, creams and gels can contain the customary excipients in addition to the active compound or compounds, for example animal and vegetable fats, waxes, paraffins, starch, tragacanth, cellulose derivatives, polyethylene glycols, silicones, bentonites, silica, talc and zinc oxide or mixtures of these substances.

Powders and sprays can contain the customary excipients in addition to the active compound or compounds, for example lactose, talc, silica, aluminium hydroxide, calcium silicate and polyamide powders or mixtures of these substances. Sprays can additionally contain the customary propellants, for example chlorofluorohydrocarbons.

Solutions and emulsions can contain the customary excipients in addition to the active compound or compounds, such as solvents, solubilising agents and emulsifiers, for example water, ethyl alcohol, isopropyl alcohol, ethyl carbonate, ethyl acetate, benzyl alcohol, benzyl benzoate, propylene glycol, 1,3-butylene glycol, dimethylformamide, oils, especially cottonseed oil, groundnut oil, maize germ oil, olive oil, castor oil and sesame oil, glycerine, glycerine-formal, tetrahydrofurfuryl alcohol, polyethylene glycols and fatty acid esters of sorbitan, or mixtures of these substances.

For parenteral administration, the solutions and emulsions can be in a sterile form which is isotonic with blood.

Suspensions can contain the customary excipients in addition to the active compound or compounds, such as liquid diluents, for example water, ethyl alcohol or propylene glycol, suspending agents, for example ethoxylated isostearyl alcohols, polyoxyethylene sorbitol esters and sorbitan esters, microcrystalline cellulose, aluminium metahydroxide, bentonite, agar-agar and tragacanth or mixtures of these substances.

The formulation forms mentioned can also contain dyestuffs, preservatives and additives which improve the odour and flavour, for example peppermint oil and eucalyptus oil, and sweeteners, for example saccharin.

The therapeutically active compounds should preferably be present in the abovementioned pharmaceutical preparations in a concentration of about 0.1 to 99.5, preferably of about 0.5 to 95, % by weight of the total mixture.

The abovementioned pharmaceutical preparations can also contain other pharmaceutical active compounds in addition to the active compounds according to the invention.

The abovementioned pharmaceutical preparations are manufactured in the usual manner according to known methods, for example by mixing the active compound or the active compounds with the excipient or excipients.

The active compounds or the pharmaceutical preparations can be administered locally, orally, parenterally, intraperitoneally and/or rectally, preferably orally or parenterally, such as intravenously or intramuscularly. In general, it has proved advantageous in medicine to administer the active compound or compounds in total amounts of about 0.5 to about 50, preferably 1 to 30, especially preferably 1-20 mg/kg of body weight, orally or parenterally, every 24 hours, optionally in the form of several individual administrations, in order to achieve the desired results. An individual administration contains the active compound or the active compounds preferably in amounts of about 1 to about 250, especially of 3 to 60, mg/kg of body weight. However, it can be necessary to deviate from the dosages mentioned and in particular to do so as a function of the nature and body weight of the subject to be treated, the nature and the severity of the illness, the nature of the preparation and of the administration of the medicine, and the time or interval over which the administration takes place. Thus it can suffice in some cases to manage with less than the abovementioned amount of active compound whilst in other cases the abovementioned amount of active compound must be exceeded. The particular required optimum dosage and the type of administration of the active compounds can easily be decided by anyone skilled in the art, on the basis of his expert knowledge.

The new compounds can be utilized as feedstuff additives and used in the customary concentrations and preparations together with the feed or with the feed preparations or with the drinking water. By this means, a promotion of growth and an improvement in the utilization of the feed can be achieved.

The preparation examples which follow illustrate the invention:

EXAMPLE A (Preparation of the starting material II):

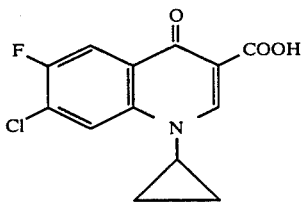

24.3 g of magnesium turnings are suspended in 50 ml of anhydrous ethanol. 5 ml of carbon tetrachloride are added and, when the reaction has started up, a mixture of 160 g of diethyl malonate, 100 ml of absolute ethanol and 400 ml of anhydrous ether is added dropwise, vigorous reflux being observed. After the reaction has moderated, the mixture is heated to boiling for 2 hours, then cooled down to −5° C. to −10° C. with dry ice-/acetone and, at this temperature, a solution of 227.5 g of 2,4-dichloro-5-fluorobenzoyl chloride (1) in 100 ml of absolute ether is slowly added dropwise. The mixture is stirred at 0° to −5° C. for 1 hour, allowed to reach room temperature overnight and, while cooling in ice, a mixture of 400 ml of ice-water and 25 ml of concentrated sulphuric acid is allowed to run in. The phases are separated and the aqueous phase is extracted twice more with ether. The combined ether solutions are washed with saturated NaCl solution, dried with $Na_2SO_4$ and the solvent is removed in vacuo. 349.5 g of diethyl 2,4-dichloro-5-fluorobenzoylmalonate (3) are obtained as a crude product.

0.15 g of p-toluenesulphonic acid is added to an emulsion of 34.9 g of crude diethyl 2,4-dichloro-5-fluorobenzoylmalonate (3) in 50 ml of water. The mixture is heated to boiling, with thorough stirring, for 3 hours, the cooled emulsion is extracted several times with methylene chloride, the combined $CH_2Cl_2$ solutions are washed once with saturated NaCl solution, dried with $Na_2SO_4$ and the solvent is distilled out in vacuo. Fractionation of the residue under high vacuum provides 21.8 g of ethyl 2,4-dichloro-5-fluorobenzoylacetate (4) of boiling point 127°–142° C./0.09 mbar.

A mixture of 21.1 g of ethyl 2,4-dichloro-5-fluorobenzoylacetate (4), 16.65 g of ethyl orthoformate and 18.55 g of acetic anhydride is heated at 150° C. for 2 hours. The volatile components are then distilled out under waterpump vacuum and finally under high vacuum at a bath temperature of 120° C. 25.2 g of crude ethyl 2-(2,4-dichloro-5-benzoyl)-3-ethoxyacrylate (5) remain behind. This is pure enough for the subsequent reactions.

4.3 g of cyclopropylamine are added dropwise, with cooling in ice and stirring, to a solution of 24.9 g of ethyl 2-(2,4-dichloro-5-fluorobenzoyl)-3-ethoxyacrylate (5) in 80 ml of ethanol. When the exothermic reaction has moderated, the mixture is stirred at room temperature for 1 hour, the solvent is removed in vacuo and the residue is recyrstallised from cyclohexane/petroleum ether. 22.9 g of ethyl 2-(2,4-dichloro-5-fluorobenzoyl)-3-cyclopropylaminoacrylate (6) of melting point 89°–90° C. are obtained.

3.44 g of 80% sodium hydride are added in portions, with cooling in ice and stirring, to a solution of 31.9 g of ethyl 2-(2,4-dichloro-5-fluorobenzoyl)-3-cyclopropylaminoacrylate (6) in 100 ml of anhydrous dioxane. The mixture is then stirred at room temperature for 30 minutes and under reflux for 2 hours and the dioxane is removed in vacuo. The residue (40.3 g) is suspended in 150 ml of water, 6.65 g of potassium hydroxide are added and the mixture is refluxed for 1.5 h. The warm solution is filtered and washed with $H_2O$. The solution is then acidified to pH 1 to 2 with half-concentrated hydrochloric acid, with cooling in ice, the precipitate is filtered off with suction, washed with water and dried in vacuo at 100° C. In this manner, 27.7 g of 7-chloro-1-cyclo-propyl-6-fluoro-1,4-dihydro-4-oxoquinoline-3-carboxylic acid II, of melting point 234°–237° C., are obtained.

EXAMPLE 1

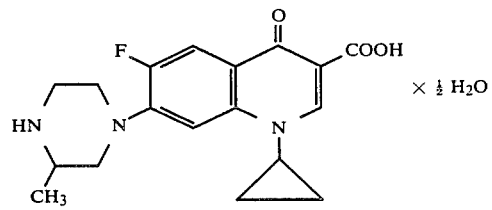

A mixture of 2.8 g (0.01 mol) of 7-chloro-1-cyclopropyl-6-fluoro-1,4-dihydro-4-oxoquinoline-carboxylic acid (II) and 5.1 g (0.051 mol) of 2-methylpiperazine in 6 ml of dimethyl sulphoxide is heated at 140° C. for 2 hours. The solvent is then distilled out under high vacuum, 6 ml of hot water are added to the residue and the mixture is kept at 95° C. for 1 hour. It is then cooled with ice, the precipitate which has separated out is filtered off, washed with a little water and dissolved in a mixture of 0.8 ml of acetic acid and 10 ml of water at 90° to 100° C. The filtrate is adjusted to pH 8 with potassium hydroxide solution (0.75 g of KOH in 0.7 ml of water) and the precipitate which has separated out is recrystallised from methanol. 1.8 g (52% of theory) of 1-cyclopropyl-6-fluoro-1,4-dihydro-4-oxo-7-(3-methyl-1-piperazinyl)quinoline-3-carboxylic acid semihydrate, with a decomposition point of 230° to 232° C., is obtained.

EXAMPLE 2

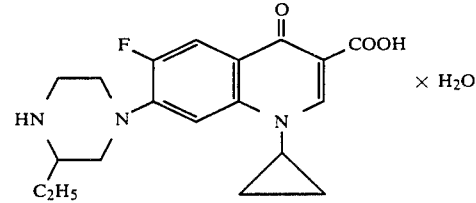

A mixture of 2.8 g (0.01 mol) of 7-chloro-1-cyclopropyl-6-fluoro-1,4-dihydro-4-oxoquinoline-3-carboxylic acid (II) and 3.4 g (0.03 mol) of 2-ethylpiperazine in 15 ml of dimethyl sulphoxide is heated at 140° C. for 2 hours. The solution is evaporated under high vacuum, the residue is heated with 30 ml of water to 90° C., the precipitate which has separated out is filtered off with suction, washed with water and methanol and isolated. 1.1 g (31% of theory) of 1-cyclopropyl-6-fluoro-1,4-dihydro-4-oxo-7-(3-ethyl-1-piperazinyl)quinoline-3-carboxylic acid monohydrate, with a decomposition point of 255°–258° C., is obtained.

EXAMPLE 3

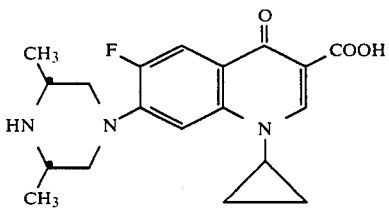

A mixture of 2.8 g (0.01 mol) of 7-chloro-1-cyclopropyl-6-fluoro-1,4-dihydro-4-oxoquinoline-3-carboxylic acid, 1.14 g (0.01 mol) of cis-2,6-dimethylpiperazine and 2.2 g of diazabicyclo[2.2.2]octane is heated at 140° C. for 5 hours. The solvent is distilled off under high vacuum, 30 ml of water are added to the residue, the suspension is adjusted to pH 8 with 2N HCl and the precipitate which has separated out is extracted by boiling with 30 ml of methanol. 0.75 g (21% of theory) of 1-cyclopropyl-6-fluoro-1,4-dihydro-4-oxo-7-(3,5-dimethyl-1-piperazinyl)quinoline-3-carboxylic acid, of decomposition point 234°–236° C., is obtained. Mass spectrum: 359 (M+), 290, 289 (100%, M+-70), 245,70.

EXAMPLE 4

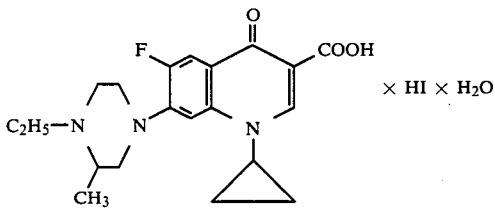

A mixture of 1.7 g (0.005 mol) of 1-cyclopropyl-6-fluoro-1,4-dihydro-4-oxo-7-(3-methyl-1-piperazinyl)-quinoline-3-carboxylic acid, 1.7 g (0.011 mol) of ethyl iodide and 1.1 g of triethylamine in 20 ml of DMF is heated at 80° C. for 3 hours. The solution is evaporated in vacuo, the crystalline residue is stirred thoroughly with 10 ml of water and the undissolved product is recrystallised from methanol. 0.6 g (32% of theory) of 1-cyclopropyl-6-fluoro-1,4-dihydro-4-oxo-7-(4-ethyl-3-methyl-1-piperazinyl)quinoline-3-carboxylic acid hydriodide monohydrate, with a decomposition point of 285°–288° C., is obtained.

EXAMPLE 5

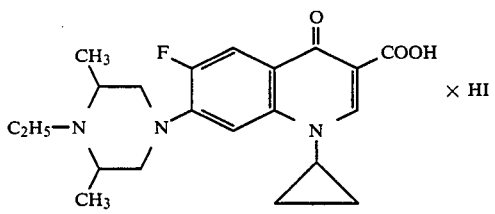

1.8 g (0.005 mol) of 1-cyclopropyl-6-fluoro-1,4-dihydro-4-oxo-7-(3,5-dimethyl-1-piperazinyl)quinoline-3-carboxylic acid is reacted in analogy to Example 4 and 0.75 g (39%) of 1-cyclopropyl-6-fluoro-1,4-dihydro-4-oxo-7-(4-ethyl-3,5-dimethyl-1-piperazinyl)quinoline-3-carboxylic acid hydriodide, with a decomposition point of 277°–279° C., is isolated.

The following compounds are obtained in analogy to Example 4:

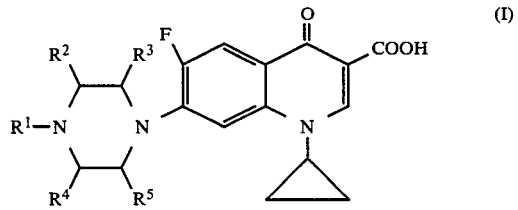

| Example | $R^1$ | Melting point |
|---|---|---|
| 6 | n-$C_3H_7$ × HBr | 293–295° C. (decomposition) |
| 7 | i-$C_3H_7$ × HI | 289–291° C. (decomposition) |
| 8 | i-$C_4H_9$ | 198–200° C. |
| 9 | n-$C_5H_9$ × HCl | 238–240° C. (decomposition) |
| 10 | n-$C_{12}H_{25}$ × HCl | 142–145° C. |
| 11 | HO—$CH_2CH_2CH_2$ | 198–201° C. (decomposition) |
| 12 | HO—$CH_2CH_2$ × HCl | 240–243° C. (decomposition) |

The minimum inhibitory concentrations (MIC) with various bacteria for some of the compounds according to the invention are given in the table below.

| Minimum inhibitory concentrations on mcg/ml in the agar dilution test; Denley multipoint inoculation procedure | | | | |
|---|---|---|---|---|
| Strain | Example 1 | Example 3 | Example 4 | Example 5 |
| E. coli Neumann | ≦0.015 | ≦0.015 | 0.03 | 0.03 |
| Klebsiella 8085 | ≦0.015 | ≦0.015 | ≦0.015 | 0.03 |
| Klebsiella 6179 | 0.125 | 0.25 | 0.25 | 0.5 |
| Klebsiella 57 USA | 0.03 | 0.125 | 0.25 | 0.5 |
| Providencia 12052 | 16 | 16 | 32 | 32 |
| Serratia 16040 | 4 | 16 | 16 | 32 |
| Staphylococcus Fk422 | 0.25 | 0.5 | 0.5 | 0.5 |
| Staphylococcus 1756 | 0.25 | 0.25 | 0.5 | 0.5 |
| Staphylococcus 133 | 0.25 | 0.25 | 0.25 | 0.5 |

We claim:
1. A 1-Cyclopropyl-6-fluoro-1,4-dihydro-4-oxo-7-(alkyl-1-piperazinyl)quinoline-3-carboxylic acid of the formula (I)

in which
$R^1$ represents hydrogen or alkyl which is optionally substituted by 1 to 2 hydroxyl and has 1 to 12 carbon atoms,
$R^2$, $R^3$, $R^4$ and $R^5$ can be identical or different and represent hydrogen or alkyl having 1 to 4 carbon atoms, at least one of the radicals $R^2$ to $R^5$ denoting alkyl, and their pharmaceutically utilisable acid addition, alkali metal and alkaline earth metal salts and hydrates.

2. A compound of claim 1, in which $R^1$ represents hydrogen or alkyl which is optionally substituted by hydroxyl and has 1 to 4 carbon atoms, $R^2$, $R^3$, $R^4$ and $R^5$ can be identical or different and represent hydrogen or alkyl having 1 or 2 carbon atoms, at least one of the radicals R² to R⁵ denoting alkyl, and their pharmaceutically utilisable acid addition, alkali metal and alkaline earth metal salts and hydrates.

3. A compound of claim 1 which is 1-Cyclopropyl-6-fluoro-1,4-dihydro-4-oxo-7-(3-methyl-1-piperazinyl)-quinoline-3-carboxylic acid.

4. A compound of claim 1 which is 1-Cyclopropyl-6-fluoro-1,4-dihydro-4-oxo-7-(3-ethyl-1-piperazinyl)-quinoline-3-carboxylic acid.

5. A compound of claim 1 which is 1-Cyclopropyl-6-fluoro-1,4-dihydro-4-oxo-7-(3,5-dimethyl-1-piperazinyl)quinoline-3-carboxylic acid.

6. A compound of claim 1 which is 1-Cyclopropyl-6-fluoro-1,4-dihydro-4-oxo-7-(4-ethyl-3-methyl-1-piperazinyl)quinoline-3-carboxylic acid.

7. A compound of claim 1 which is 1-Cyclopropyl-6-fluoro-1,4-dihydro-4-oxo-7-(4-ethyl-3,5-dimethyl-1-piperazinyl)quinoline-3-carboxylic acid.

8. A compound of claim 1 which is 1-Cyclopropyl-6-fluoro-1,4-dihydro-4-oxo-7-(4-hydroxyethyl-3-methyl-1-piperazinyl)quinoline-3-carboxylic acid.

9. A pharmaceutical composition containing as active ingredient an antibacterially effective amount of a compound of claim 1 together with an inert pharmaceutical carrier.

10. A pharmaceutical composition of claim 9 in the form of a sterile or physiologically isotonic aqueous solution.

11. A composition of claim 9 containing from 0.5 to 95% by weight of the said active ingredient.

12. A pharmaceutical composition in dosage unit form containing an antibacterially effective amount of a compound according to claim 1 and an inert pharmaceutical carrier.

13. A composition of claim 12 in the form of tablets, pills, dragees, capsules, ampoules or suppositories.

14. A method of combatting bacterial infection in a warm-blooded animal which comprises administering to said animal an antibacterially effective amount of an active compound of claim 1 in admixture with an inert pharmaceutical carrier.

15. A method of claim 14 wherein the active compound is administered in an amount of about 1 to about 250 mg/kg of body weight per day.

16. A feedstuff additive composition comprising an amount effective for growth promotion or feed utilization of an active compound of claim 1 together with an animal feed or drinking water.

* * * * *